US011484077B1

(12) United States Patent
Arsenault (10) Patent No.: US 11,484,077 B1
(45) Date of Patent: Nov. 1, 2022

(54) COMBINATION STORAGE AND STERILIZATION DEVICE FOR FAKE EYELASHES

(71) Applicant: Mea Madamba Arsenault, Tacoma, WA (US)

(72) Inventor: Mea Madamba Arsenault, Tacoma, WA (US)

( * ) Notice: Subject to any disclaimer, the term of this patent is extended or adjusted under 35 U.S.C. 154(b) by 0 days.

(21) Appl. No.: 16/596,308

(22) Filed: Oct. 8, 2019

(51) Int. Cl.
| | |
|---|---|
| *A41G 5/02* | (2006.01) |
| *A45C 11/00* | (2006.01) |
| *A45C 15/04* | (2006.01) |
| *A61L 2/10* | (2006.01) |
| *A61L 2/24* | (2006.01) |
| *A61L 2/26* | (2006.01) |

(52) U.S. Cl.
CPC .............. *A41G 5/02* (2013.01); *A45C 11/008* (2013.01); *A45C 15/04* (2013.01); *A61L 2/10* (2013.01); *A61L 2/24* (2013.01); *A61L 2/26* (2013.01); *A61L 2202/11* (2013.01); *A61L 2202/121* (2013.01); *A61L 2202/122* (2013.01); *A61L 2202/16* (2013.01); *A61L 2202/21* (2013.01)

(58) Field of Classification Search
CPC ......... A45G 5/02; A45C 11/008; A45C 15/04; A61L 2/10; A61L 2/24; A61L 2/26; A61L 2202/11; A61L 2202/121; A61L 2202/122; A61L 2202/16; A61L 2202/21
USPC .......................... 250/453.11, 454.11, 455.11
See application file for complete search history.

(56) References Cited

U.S. PATENT DOCUMENTS

| 2009/0075964 A1* | 3/2009 | Jennings-White ... C11D 3/0068 514/182 |
|---|---|---|
| 2022/0142896 A1* | 5/2022 | Kahvejian .............. A61Q 19/08 |

* cited by examiner

*Primary Examiner* — Nicole M Ippolito
(74) *Attorney, Agent, or Firm* — Leavitt Eldredge Law Firm (57) ABSTRACT

A combination storage and sterilization device for fake eyelashes is a portable device that houses and disinfects all types of fake eyelashes including eyelash extensions and eyelash tools. The device includes a casing, a drawer, a cover, and a sterilization mechanism. The sterilization mechanism may include a UV bulb, a power source such as batteries, and a control circuit with a timer to automatically turn on and off the sterilization mechanism. The device may further include additional compartments for storing tools and accessories associated with fake eyelashes.

17 Claims, 9 Drawing Sheets

COMBINATION STORAGE AND STERILIZATION DEVICE FOR FAKE EYELASHES

BACKGROUND

1. Field of the Invention

The present invention relates generally to cosmetic storage devices, and more specifically, to a combination storage and sterilization device for all types of fake eyelashes including eyelash extensions and eyelash tools.

2. Description of Related Art

Cosmetic storage devices are well known in the art and are effective means to store cosmetic products used for personal care.

One of the problems commonly associated with cosmetic storage devices is the lack of hygienic storage means. For example, fake eyelashes are prone to cause eye infections and dry eye syndrome in a user if not properly sterilized and hygienically stored.

Accordingly, although great strides have been made in the area of cosmetic storage devices, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

Embodiments of the invention are discussed below with reference to the Figures. However, those skilled in the art will readily appreciate that the detailed description given herein with respect to these figures is for explanatory purpose as the invention extends beyond these limited embodiments. For example, it should be appreciated that those skilled in the art will, in light of the teachings of the present invention, recognize a multiplicity of alternate and suitable approaches; depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" includes the stated particular feature, structure, or characteristic.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional cosmetic storage devices, Specifically, a user can both sterilize fake eyelashes and hygienically store the fake eyelashes for subsequent use. The system also allows for the sterilization of eyelash tools as well as allows for storage of said tools. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Unless defined otherwise, fake eyelashes encompasses all foreign eyelash types that are applied on or around ones natural lash and is made of material commonly understood by one of ordinary skill in the art to which this invention belongs, including but not limited to strip lashes, magnetic lashes, magnetic lash liner, eyelash extensions, that are made from mink, human hair, synthetic material, horse hair, other types of animal hair, etc. Any application of fake eyelashes, preferred methods, techniques, devices, and materials are described, although any methods, techniques, devices, or materials similar or equivalent to those described herein may be used in the practice or testing of the present invention. Structures described herein are to be understood also to refer to functional equivalents of such structures.

References to a "device," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicant hereby gives notice that new Claims may be formulated to such features and/or combinations of such features during the prosecution of the present Application or of any further Application derived therefrom.

As is well known to those skilled in the art many careful considerations and compromises typically must be made when designing for the optimal manufacture of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Figure 1:
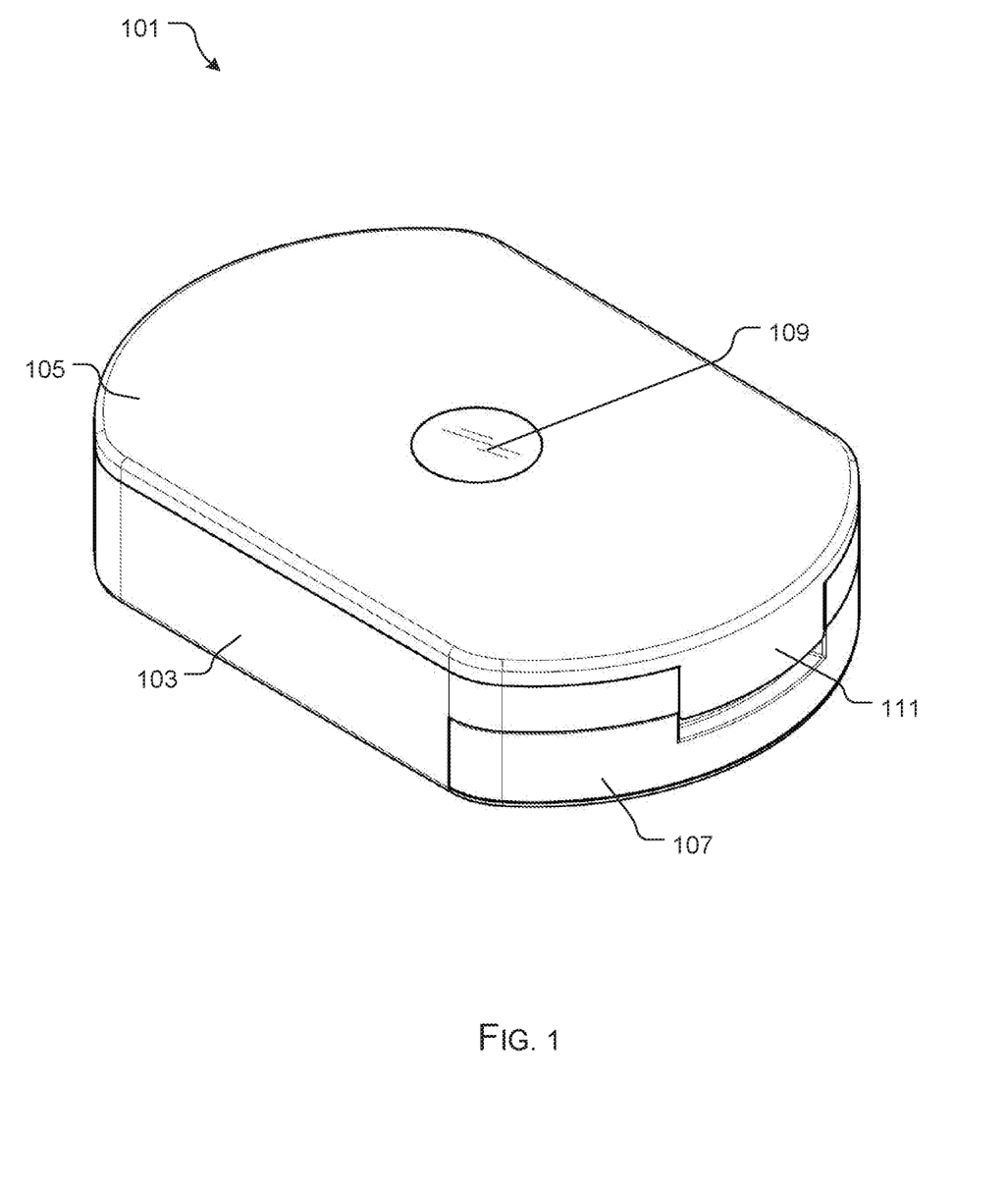
FIG. 1 is a perspective view of a combination storage and sterilization device for fake eyelashes and eyelash tools in accordance with a preferred embodiment of the present application.

Referring now to the drawings wherein like reference characters identify corresponding or similar elements throughout the several views, FIG. 1 depicts a perspective view of a combination storage and sterilization device for fake eyelashes in accordance with a preferred embodiment of the present application. It will be appreciated that system 101 overcomes one or more of the above-listed problems commonly associated with conventional cosmetic storage systems.

Figure 2:
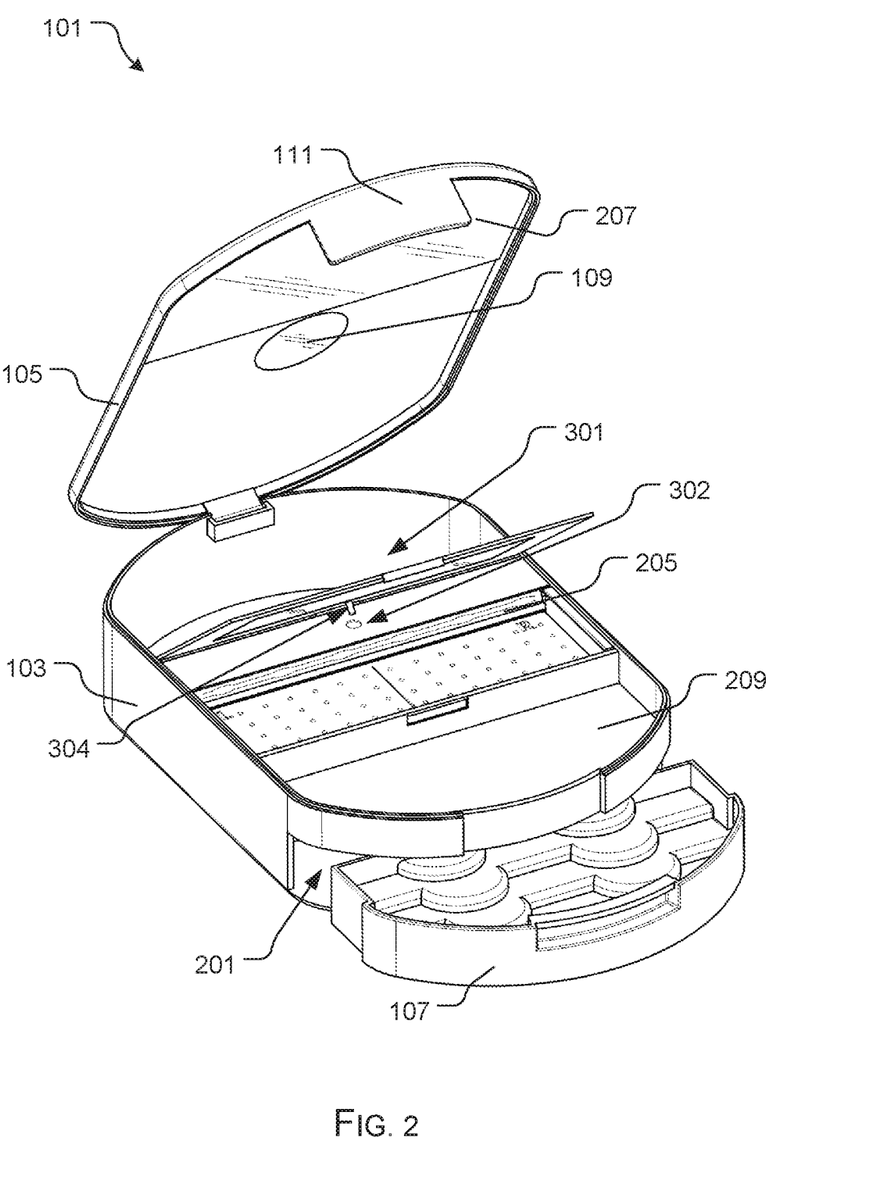
FIG. 2 is a perspective view of the device of FIG. 1 in a cover open configuration.
Figure 3:
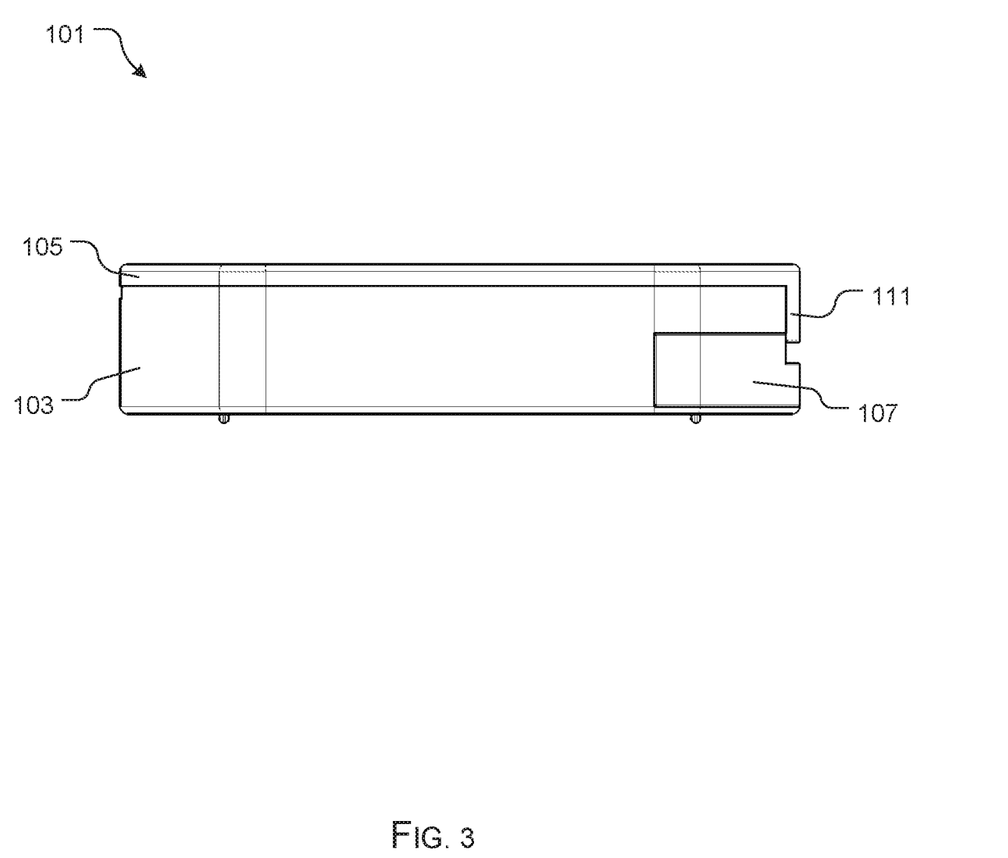
FIG. 3 is a side view of the device in FIG. 1 in a cover closed configuration.

In the contemplated embodiment, system 101 includes a casing 103, a cover 105, a drawer 107, and a sterilization mechanism 205. The casing 103 has a drawer cavity 201 and a sterilization cavity 203. The casing 103 may include a plurality of additional cavities 209 and 301 for storing tools and accessories associated with fake eyelashes as shown in FIG. 2. The drawer 107 may have a drawer open configuration and a drawer closed configuration such as by sliding into and out of the drawer cavity 201.

The cover 105 may include a window 109 that allows light to pass through while the device 101 and the sterilization lid 703 is in the cover closed configuration. Device 101 may further include a locking mechanism 111 such as a latch or the like for securing the cover 105 over the casing 103 as shown in FIG. 1. The cover may also include a mirror 207 allowing the user to apply the fake eyelashes without the need for a separate mirror as shown in FIG. 2.

Figure 4:
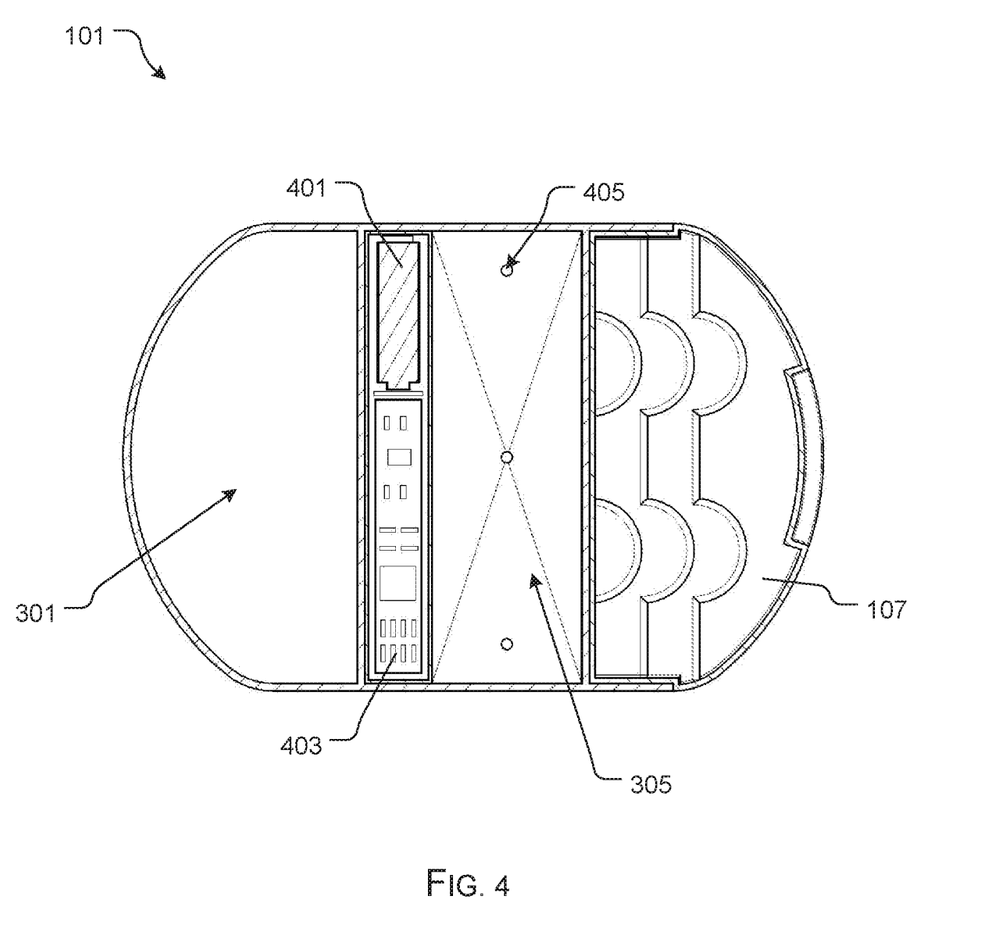
FIG. 4 is a top view of the device in FIG. 1 in the cover open configuration.
Figure 5:
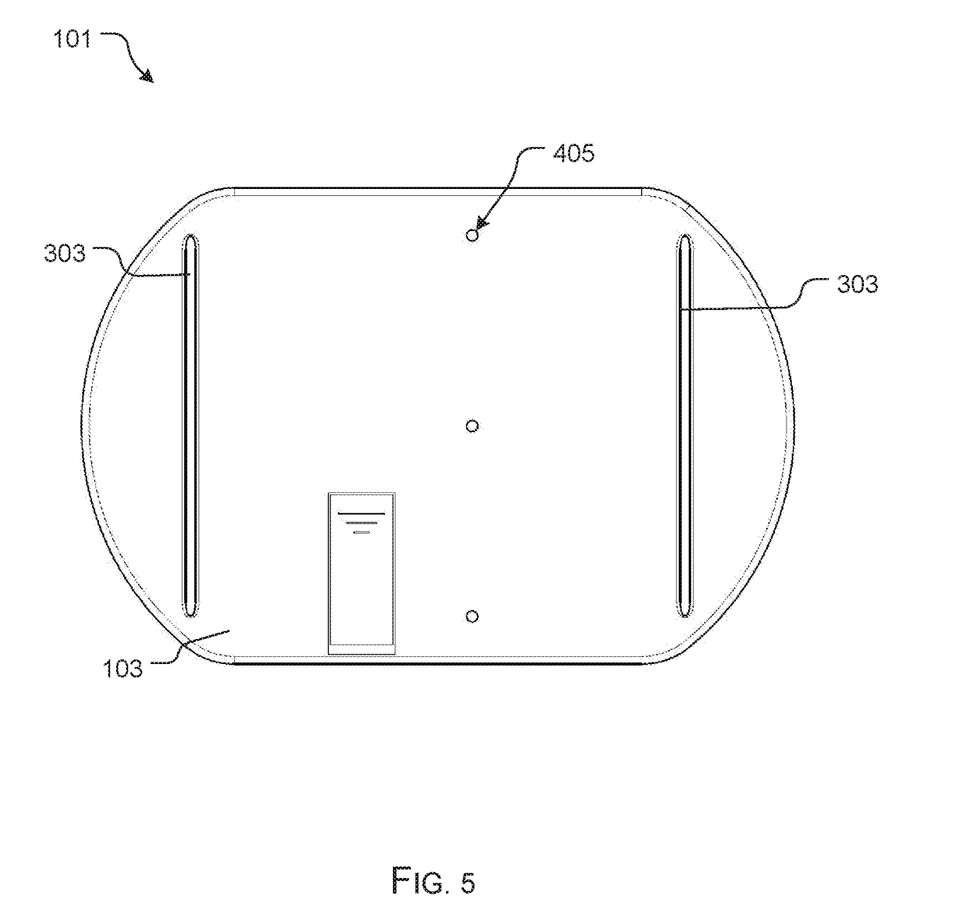
FIG. 5 is a bottom view of the device in FIG. 1.
Figure 6:
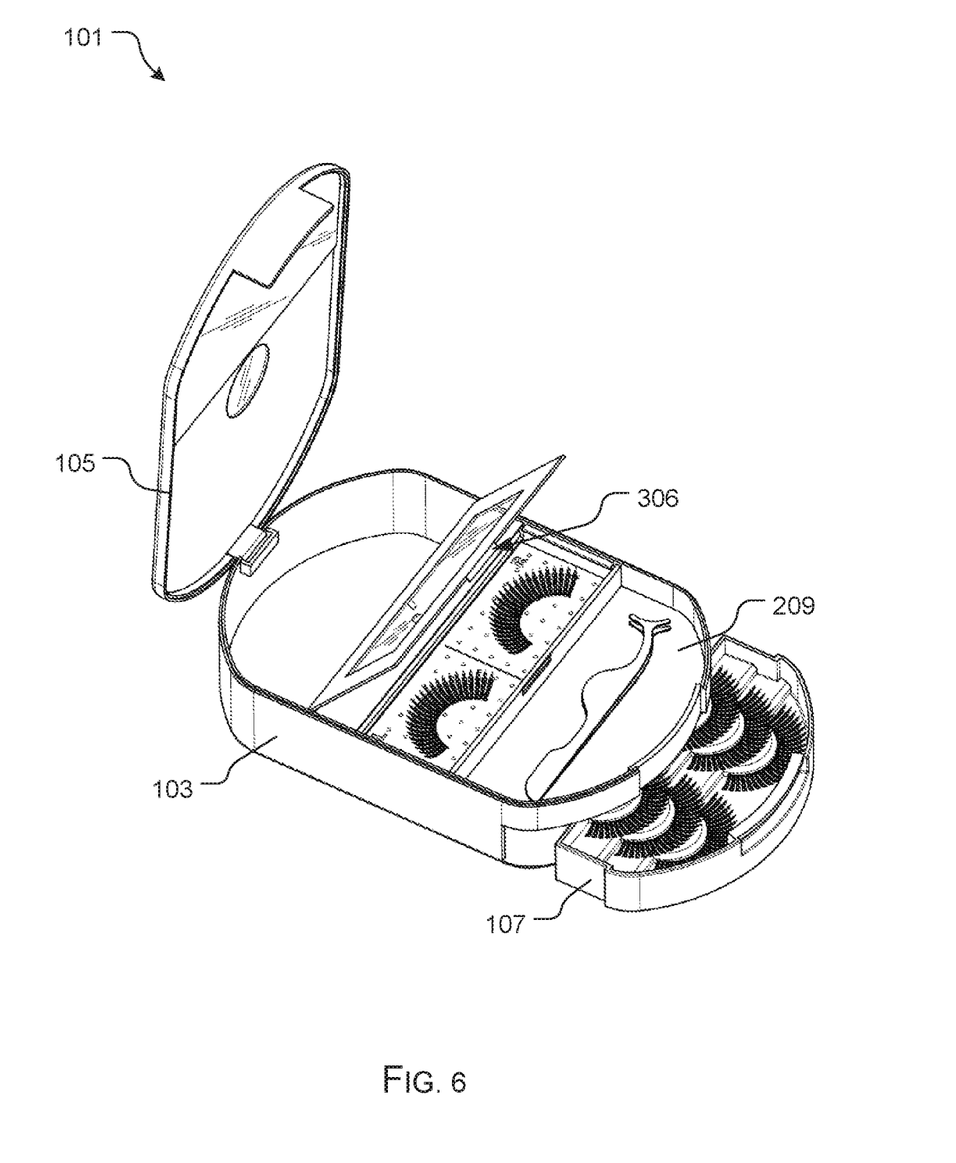
FIG. 6 is a perspective view of the device in FIG. 1 in the cover open configuration and in use with fake eyelashes.
Figure 9:
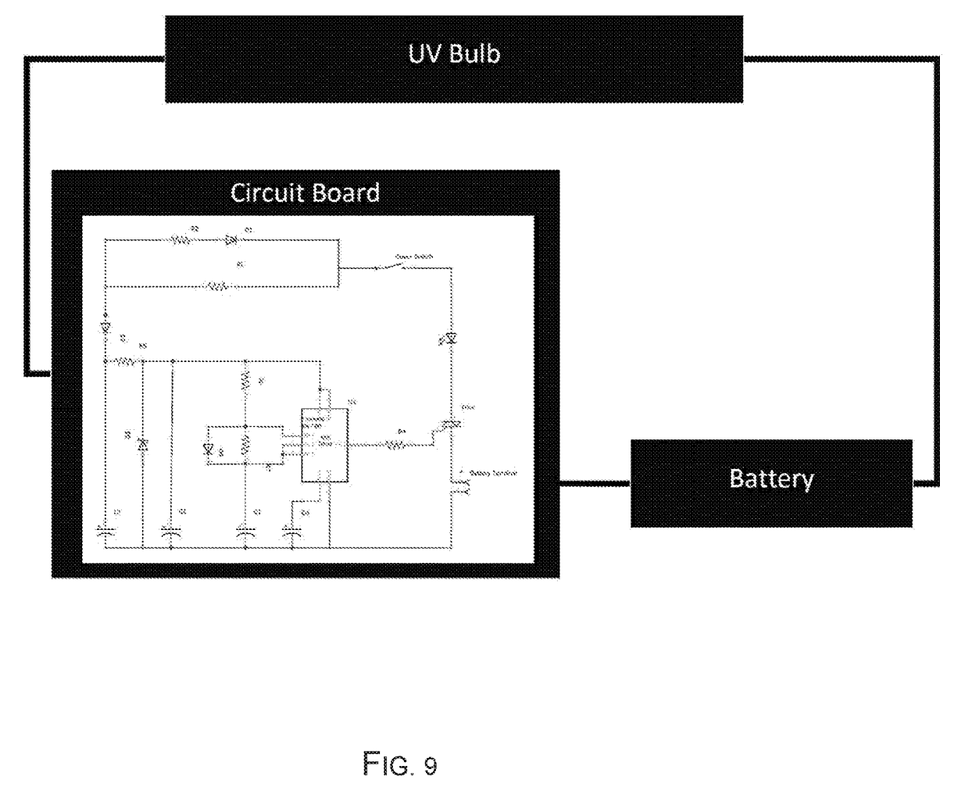
FIG. 9 is a control circuit of the device in FIG. 1.

The sterilization mechanism 205 is housed within the sterilization cavity 203. The sterilization mechanism may be a UV light source or similar form of sterilization. The device 101 may also include a power source 401 to provide power to the sterilization mechanism 205. The power source 401 may be a plurality of batteries or plugged directly into a socket or a combination. The device 101 may further include a control circuit 403 connected to the power source 401 and the sterilization mechanism 205 and may be configured with the use of a timer to automatically turn on and off the sterilization mechanism 205. 304 is a lever that activates the control circuit through the hole 302 which turns on the sterilization unit mechanism 205 and after a defined amount of time the sterilization mechanism 205 shuts off automatically as determined by the timer on the control circuit 403. The device 101 may also include a drain 405 such as holes in the bottom of the device 101 or similar drainage system for assisting in evaporation and drainage of water droplets that passed through the removeable drip tray 203 which is enclosed in the casing 103 as shown in FIG. 4 and FIG. 5. The support legs 303 help assist with the drainage system raising the device 101 so as not to sit flush on any flat surface whereby keeping the drains 405 exposed.

Figure 7:
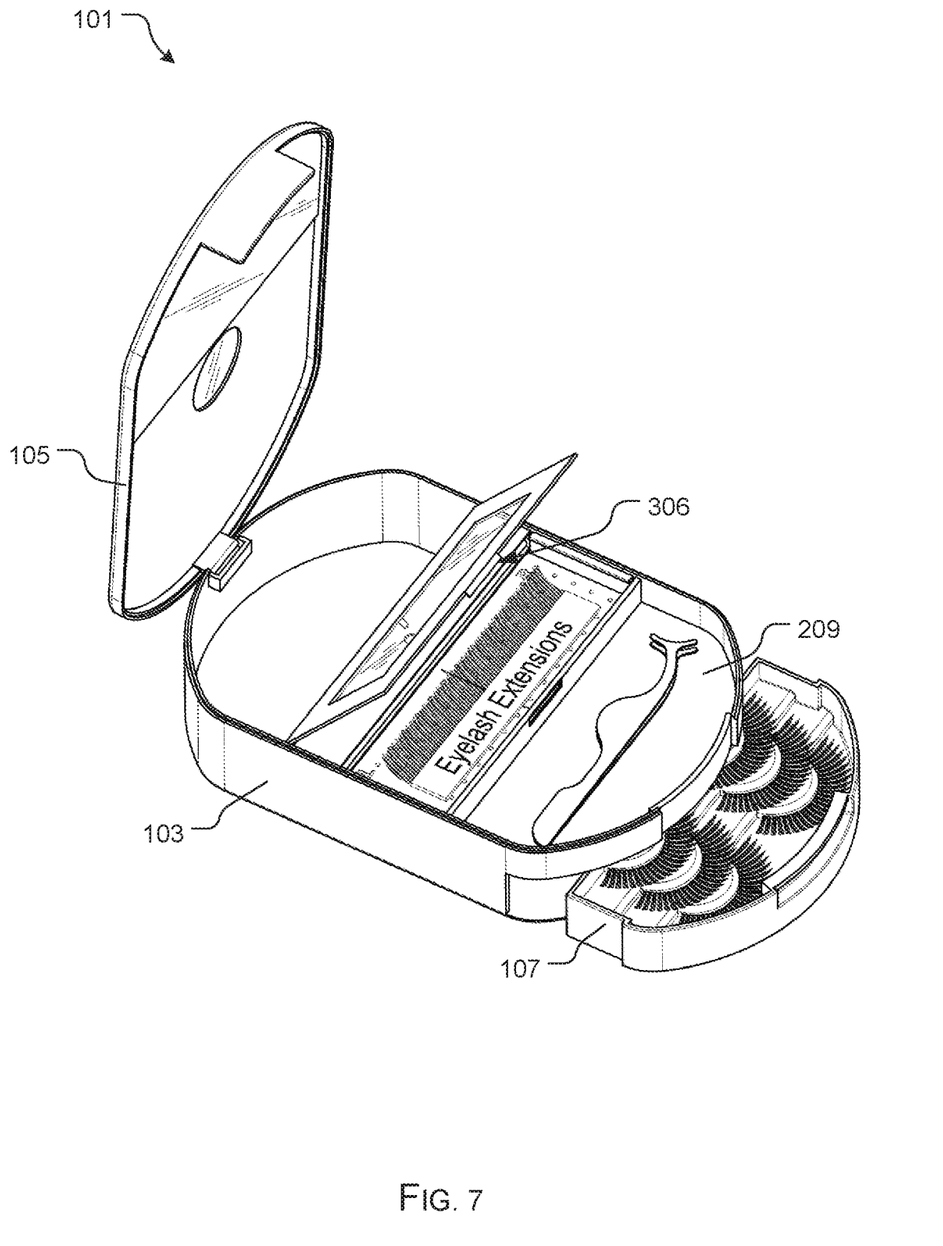
FIG. 7 is a perspective view of the device in FIG. 1 in the cover open configuration and in use with fake eyelash extensions.
Figure 8:
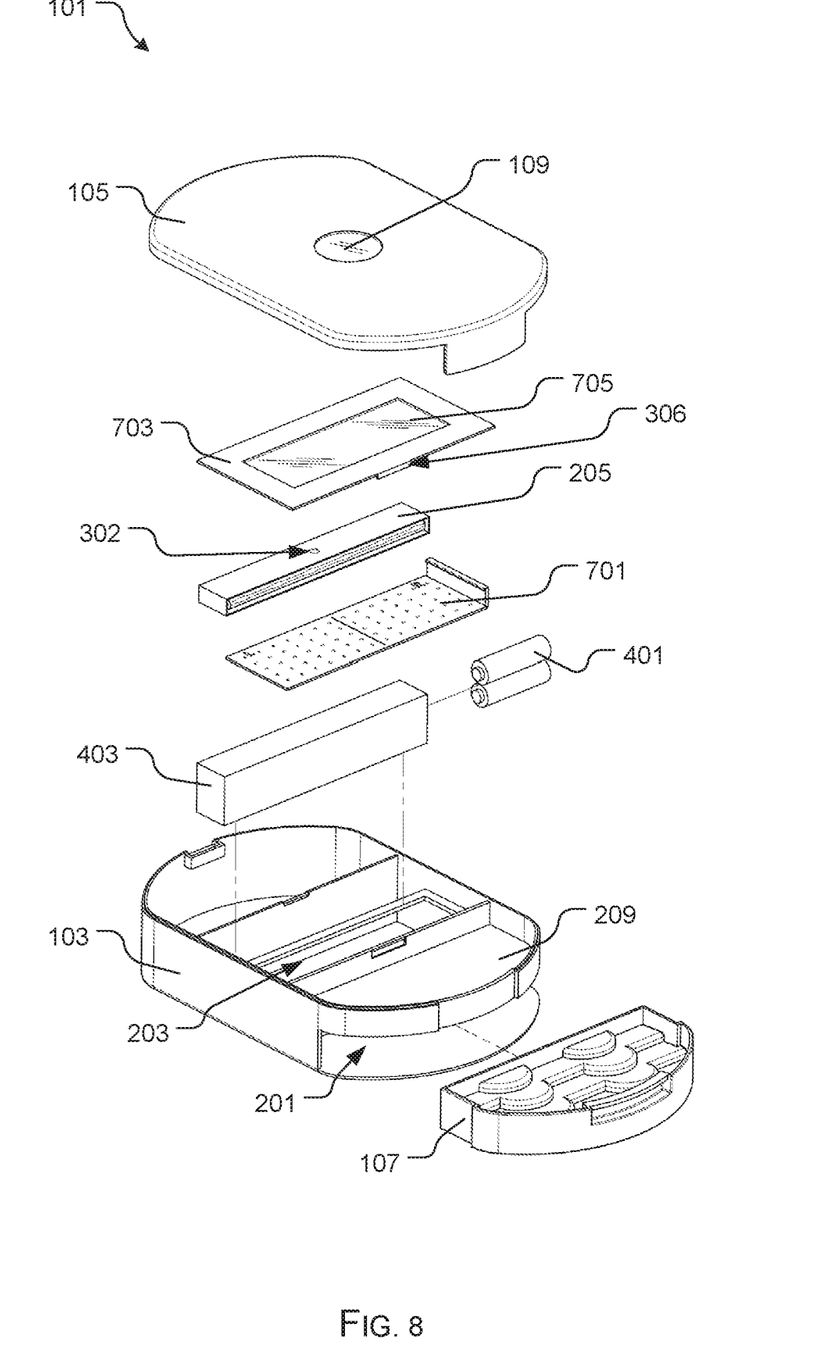
FIG. 8 is an exploded view of the device in FIG. 1.

The device 101 may further include a sterilization lid 703 connected to the sterilization cavity 203 allowing the sterilization cavity 203 to be sealed separately from the casing 103. The sterilization lid 703 may include a sterilization window 705. The device 101 may further include a removable drip tray 701 housed within the sterilization cavity 203, which would allow access to the bottom of the device 101 drainage basin 305 for easy cleaning. The removeable drip tray 701 may be visually separated into two sides such as a "left" side and a "right" side and may have a plurality of holes allowing water to pass through to the drainage basin 305 below.

It should be appreciated that one of the unique features believed characteristic of the present application is the combination of storage and a sterilization mechanism for fake eyelashes as well as fake eyelash tools into a single device.

The device 101 may be compact making it easy for the user to carry around while traveling. The device 101 may also be a larger container that is mobile such as on wheels and may be useful for larger events such as for a makeup artist or a wedding party or the like. The device 101 may also have different configurations allowing for the sterilization of a plurality of fake eyelashes and/or eyelash tools in combination, as well as store a plurality of additional fake eyelashes and eyelash tools and supplies. The device 101 may also be stationary incorporated into furnishings or intended to sit atop a shelf.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

It is noted that according to USA law 35 USC § 112 (1), all claims must be supported by sufficient disclosure in the present patent specification, and any material known to those skilled in the art need not be explicitly disclosed. However, 35 USC § 11 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any 3rd parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing cosmetic storage devices, and more specifically, to a combination storage and sterilization device for all types of fake eyelashes (including eyelash extensions) and eyelash tools according to the present invention will be apparent to those skilled in the art. Various aspects of the invention have been described above by way of illustration, and the specific embodiments disclosed are not intended to limit the invention to the particular forms disclosed. The particular implementation of storage and sterilization of fake eyelashes and eyelash tools may vary depending upon the particular context or application. By way of example, and not limitation, the device 101 described in the foregoing were principally directed to storing and sterilizing all types of fake eyelashes and eyelash tools; however, similar techniques may instead be applied to additional cosmetic tools requiring sterilization and storage other than those related specifically to fake eyelashes or eyelash tools. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

What is claimed is:

1. A combination storage and sterilization device for fake eyelashes and fake eyelash tools, comprising:
    a casing having:
        a drawer cavity; and
        a sterilization cavity;
    a drawer configured to fit within the drawer cavity enabling a drawer open configuration and a drawer closed configuration;
    a cover attached to the casing enabling a cover open configuration and a cover closed configuration; and
    a sterilization mechanism housed within the sterilization cavity enabling a cover open configuration and a cover closed configuration.

2. The combination storage and sterilization device for fake eyelashes and fake eyelash tools of claim 1, further comprising a power source connected to the sterilization mechanism and configured to provide power to the sterilization mechanism.

3. The combination storage and sterilization device for fake eyelashes and fake eyelash tools of claim 2, wherein the power source is a plurality of batteries.

4. The combination storage and sterilization device for fake eyelashes and fake eyelash tools of claim 2, wherein the power source is provided by plugging the device directly into a socket.

5. The combination storage and sterilization device for fake eyelashes and fake eyelash tools of claim 2, further comprising a circuit connected to the sterilization mechanism and the power source, the circuit having a timer and an invertor and configured to automatically turn on and off the sterilization mechanism.

6. The combination storage and sterilization device for fake eyelashes and fake eyelash tools of claim 1, wherein the casing further comprises a plurality of storage cavities configured to house tools and accessories associated with fake eyelashes.

7. The combination storage and sterilization device for fake eyelashes and fake eyelash tools of claim 1, wherein the sterilization mechanism is a UV light source.

8. The combination storage and sterilization device for fake eyelashes and fake eyelash tools of claim 1, further comprising a removeable drip tray housed within the sterilization cavity.

9. The combination storage and sterilization device for fake eyelashes and fake eyelash tools of claim 8, wherein the removeable drip tray is visually separated into two sides.

10. The combination storage and sterilization device for fake eyelashes and fake eyelash tools of claim 1, further comprising a drain configured to assist with evaporation and water drainage.

11. The combination storage and sterilization device for fake eyelashes and fake eyelash tools of claim 10, further comprising support legs.

12. The combination storage and sterilization device for fake eyelashes and fake eyelash tools of claim 1, wherein the cover has a mirror.

13. The combination storage and sterilization device for fake eyelashes and fake eyelash tools of claim 1, further comprising a locking mechanism configured to secure the cover in the cover closed configuration.

14. The combination storage and sterilization device for fake eyelashes and fake eyelash tools of claim 1, further comprising a sterilization lid attached to the sterilization cavity enabling a sterilization lid open configuration and a sterilization lid closed configuration.

15. The combination storage and sterilization device for fake eyelashes and fake eyelash tools of claim 14, wherein the sterilization lid has a sterilization window.

16. The combination storage and sterilization device for fake eyelashes and fake eyelash tools of claim 14, further comprising a sterilization locking mechanism configured to secure the sterilization lid in the cover closed configuration.

17. The combination storage and sterilization device for fake eyelashes and fake eyelash tools of claim 1, wherein the cover has a window configured to allow light to pass through while both the cover and the sterilization lid are in the cover closed configuration.

* * * * *